(12) United States Patent
Valoir (10) Patent No.: US 8,986,003 B2
(45) Date of Patent: Mar. 24, 2015

(54) PEARLESCENT WHITE ALIGNERS

(71) Applicant: OrthoAccel Technologies Inc., Bellaire, TX (US)

(72) Inventor: Tamsen Valoir, Houston, TX (US)

(73) Assignee: OrthoAccel Technologies, Inc., Bellaire, TX (US)

( * ) Notice: Subject to any disclaimer, the term of this patent is extended or adjusted under 35 U.S.C. 154(b) by 0 days.

(21) Appl. No.: 13/951,242

(22) Filed: Jul. 25, 2013

(65) Prior Publication Data

US 2014/0072926 A1    Mar. 13, 2014

Related U.S. Application Data (60) Provisional application No. 61/700,643, filed on Sep. 13, 2012.

(51) Int. Cl.
    *A61C 7/08*   (2006.01)
(52) U.S. Cl.
    CPC ........................................ *A61C 7/08* (2013.01)
    USPC ................................................. 433/6; 433/24
(58) Field of Classification Search
    CPC ............... A61C 7/08; A61C 7/10; A61C 7/36
    USPC .................................................. 433/6, 18, 24
    See application file for complete search history.

(56) References Cited

U.S. PATENT DOCUMENTS

| | | | |
|---|---|---|---|
| 3,660,900 A | 5/1972 | Andrews | |
| 3,860,803 A | 1/1975 | Levine | |
| 4,141,144 A * | 2/1979 | Lustgarten | 433/217.1 |
| 4,348,178 A * | 9/1982 | Kurz | 433/6 |
| 4,433,959 A | 2/1984 | Faunce | |
| 4,475,892 A | 10/1984 | Faunce | |
| 4,505,673 A * | 3/1985 | Yoshii | 433/6 |
| 4,755,139 A | 7/1988 | Abbatte | |
| 4,798,534 A | 1/1989 | Breads | |
| 4,856,991 A | 8/1989 | Breads | |
| 4,936,862 A | 6/1990 | Walker | |
| 5,009,709 A | 4/1991 | Ibsen | |
| 5,011,405 A | 4/1991 | Lemchen | |
| 5,035,613 A | 7/1991 | Breads | |
| 5,055,039 A | 10/1991 | Abbatte | |
| 5,059,118 A | 10/1991 | Breads | |
| 5,089,455 A | 2/1992 | Ketcham | |
| 5,139,419 A | 8/1992 | Andreiko | |
| 5,186,623 A | 2/1993 | Breads | |
| 5,273,429 A | 12/1993 | Rekow | |
| 5,338,198 A | 8/1994 | Wu | |
| 5,340,309 A | 8/1994 | Robertson | |
| 5,342,202 A | 8/1994 | Deshayes | |

(Continued)

FOREIGN PATENT DOCUMENTS

WO     2013155366     10/2013

OTHER PUBLICATIONS

Novant Pigments "Novant Sirius pearlescent pigments". Feb, 15, 2008; accesed via Internet Archieve Wayback Machine. http://www.novantchemicals.com/nspp.html.*

(Continued)

*Primary Examiner* — Edward Moran
(74) *Attorney, Agent, or Firm* — Boulware & Valoir (57) ABSTRACT

Improved aligners are provided with pearlescent white coloring and improved aesthetics.

16 Claims, 4 Drawing Sheets

(56) References Cited

U.S. PATENT DOCUMENTS

| | | | |
|---|---|---|---|
| 5,368,478 | A | 11/1994 | Andreiko |
| 5,382,164 | A | 1/1995 | Stern |
| 5,395,238 | A | 3/1995 | Andreiko |
| 5,431,562 | A | 7/1995 | Andreiko |
| 5,447,432 | A | 9/1995 | Andreiko |
| 5,452,219 | A | 9/1995 | Dehoff |
| 5,454,717 | A | 10/1995 | Andreiko |
| 5,474,448 | A | 12/1995 | Andreiko |
| 5,533,895 | A | 7/1996 | Andreiko |
| 5,549,476 | A | 8/1996 | Stern |
| 5,587,912 | A | 12/1996 | Andersson |
| 5,605,459 | A | 2/1997 | Kuroda |
| 5,607,305 | A | 3/1997 | Andersson |
| 5,645,421 | A | 7/1997 | Slootsky |
| 5,741,355 | A * | 4/1998 | Yamamoto et al. ............ 106/417 |
| 6,299,440 | B1 * | 10/2001 | Phan et al. ...................... 433/24 |
| 6,354,144 | B1 | 3/2002 | Hirota |
| 6,471,511 | B1 | 10/2002 | Chishti |
| 6,682,346 | B2 | 1/2004 | Chishti |
| 6,699,037 | B2 | 3/2004 | Chishti |
| 6,797,767 | B2 | 9/2004 | Stannard |
| 6,899,948 | B2 | 5/2005 | Zhang |
| 7,186,115 | B2 * | 3/2007 | Goldberg et al. ............. 433/18 |
| 7,214,262 | B2 * | 5/2007 | Hurwitz et al. ................ 106/35 |
| 7,229,286 | B2 | 6/2007 | Jones |
| 7,481,121 | B1 | 1/2009 | Cao |
| 2008/0227046 | A1 | 9/2008 | Lowe |
| 2008/0227047 | A1 | 9/2008 | Lowe |
| 2009/0047633 | A1 | 2/2009 | Huo |
| 2009/0191503 | A1 | 7/2009 | Matov |
| 2010/0055634 | A1 | 3/2010 | Spaulding |
| 2010/0055635 | A1 | 3/2010 | Kakavand |
| 2011/0136070 | A1 | 6/2011 | Rubin |
| 2012/0040300 | A1 | 2/2012 | Levens |
| 2013/0059263 | A1 | 3/2013 | Lowe |

OTHER PUBLICATIONS

Novant Pigments "Plastics". Feb. 15, 2008; accessed via Internet Archieve Wayback Machine. http://www.novantchemicals.com/plastics.html.*

Meng Z, et al., Measurement of the refractive index of human teeth by optical coherence tomography, J Biomed Opt. 14(3):034010 (2009).

Klages, U., et al., American Journal of Orthodontics and Dentofacial Orthopedics 128(4): 442-449 (2005).

Tarazzo et al., Comparison of retentive systems for composites used as alternatives to porcelain in fixed partial dentures The Journal of Prosthetic Dentistry 89(6): 572-578 (2003).

Pini N., et al., Advances in dental veneers: materials, applications, and techniques, Clinical, Cosmetic and Investigational Dentistry 4:9-16 (2012).

* cited by examiner

PEARLESCENT WHITE ALIGNERS

PRIOR RELATED APPLICATIONS

This application claims priority to 61/700,643, filed Sep. 13, 2012, and expressly incorporated by reference in its entirety.

FEDERALLY SPONSORED RESEARCH STATEMENT

Not applicable.

FIELD OF THE INVENTION

This invention relates to aligners used for orthodontic remodeling.

BACKGROUND OF THE INVENTION

A malocclusion is a misalignment of teeth or incorrect relation between the teeth of the two dental arches. The term was coined by Edward Angle—the father of modern orthodontics—as a derivative of occlusion, which refers to the way opposing teeth meet. Angle based his classifications of malocclusions on the relative position of the maxillary first molar. According to Angle, the mesiobuccal cusp of the upper first molar should align with the buccal groove of the mandibular first molar. The teeth should all fit on a line of occlusion, which is a smooth curve through the central fossae and cingulum of the upper canines, and through the buccal cusp and incisal edges of the mandible. Any variations therefrom results in malocclusion.

There are three classes of malocclusions, Class I, II, and III. Further, class II is subdivided into three subtypes:

Class I: Neutrocclusion Here the molar relationship of the occlusion is normal or as described for the maxillary first molar, but the other teeth have problems like spacing, crowding, over or under eruption, etc.

Class II: Distocclusion (retrognathism, overjet) In this situation, the upper molars are placed not in the mesiobuccal groove, but anteriorly to it. Usually the mesiobuccal cusp rests in between the first mandibular molars and second premolars. There are two subtypes:

Class II Division 1: The molar relationships are like that of Class II and the anterior teeth are protruded.

Class II Division 2: The molar relationships are class II but the central incisors are retroclined and the lateral incisors are seen overlapping the central incisors.

Class III: Mesiocclusion (prognathism, negative overjet) In this case the upper molars are placed not in the mesiobuccal groove, but posteriorly to it. The mesiobuccal cusp of the maxillary first molar lies posteriorly to the mesiobuccal groove of the mandibular first molar. This malocclusion is usually seen when the lower front teeth are more prominent than the upper front teeth. In such cases, the patient very often has either a large mandible or a short maxillary bone.

Orthodontics, formerly orthodontia (from Greek orthos "straight or proper or perfect"; and odous "tooth"), is the first specialty of dentistry that is concerned with the study and treatment of malocclusion, which can be a result of tooth irregularity, disproportionate facial skeleton relationship, or both. Orthodontics treats malocclusion through the displacement of teeth via bony remodeling and control and modification of facial growth.

This process has been traditionally accomplished by using static mechanical force to induce bone remodeling, thereby enabling teeth to move. In this approach, braces consisting of an archwire interfaces with brackets that are affixed to each tooth. As the teeth respond to the pressure applied via the archwire by shifting their positions, the wires are again tightened to apply additional pressure. This widely accepted approach to treating malocclusion takes about twenty four months on average to complete, and is used to treat a number of different classifications of clinical malocclusion.

Treatment with braces is complicated by the fact that it is uncomfortable and/or painful for patients, and the orthodontic appliances are perceived as unaesthetic, all of which creates considerable resistance to use. Further, the treatment time cannot be shortened by increasing the force, because too high a force results in root resorption, as well as being more painful. The average treatment time of 24-months is very long, and further reduces usage. In fact, some estimates provide that less than half of the patients who could benefit from such treatment elect to pursue orthodontics.

Kesling introduced the tooth positioning appliance in 1945 as a method of refining the final stage of orthodontic finishing after removal of the braces (debanding). The positioner was a one-piece pliable rubber appliance fabricated on the idealized wax set-ups for patients whose basic treatment was complete. Kesling also predicted that certain major tooth movements could also be accomplished with a series of positioners fabricated from sequential tooth movements on the set-up as the treatment progressed. However, this idea did not become practical until the advent of 3D scanning and computer modeling in 1997, when the Invisalign® system was introduced by Align Technologies®.

Removable clear appliances, such as Invisalign®, OrthoClear®, ClearAligner® and ClearCorrect®, provide greatly improved aesthetics since the devices are transparent. However, because these appliances can be removed, compliance can be an issue, and failure to use the device slows overall treatment time. The success of clear aligners is predicated on a patient's commitment to wear the aligners for a minimum of 20-22 hours per day, only removing them to eat, drink, and brush the teeth.

As a treatment modality, aligners are also limited in the classifications of clinical malocclusion that they can address. In the past, aligners have not been able to easily rotate or extrude teeth because the aligner cannot adequately direct force in all directions. Conditions that can be difficult to treat or are contra-indicated for treatment with clear aligners include:
  crowding and spacing over 5 mm
  skeletal anterior-posterior discrepancies of more than 2 mm (as measured by discrepancies in cuspid relationships)
  centric-relation and centric-occlusion discrepancies
  severely rotated teeth (more than 20 degrees)
  open bites (anterior and posterior) that need to be closed
  extrusion of teeth
  severely tipped teeth (more than 45 degrees)
  teeth with short clinical crowns
  arches with multiple missing teeth.

Being aware of the aligner limitations, Align Technologies® has recently combined the clear aligners with clear attachments or posts that adhere to teeth and provide a surface on which force can be exerted in the desired direction. A custom mold is made using a 3D model of the patients teeth with pockets therein for the placement of a force attachment, the placement and shape of which are determined using proprietary modeling software. The relevant force attachments are made and fitted into the mold, adhesive applied to the attachments, and the mold applied to the teeth. This allows precise and quick placement of the clear attachments, which are then affixed using light curing of the adhesive. These attachments allow the Invisalign® to tackle some of the more difficult orthodontic problems, including directing force to a tooth that needs to be further extruded.

Figure 1:
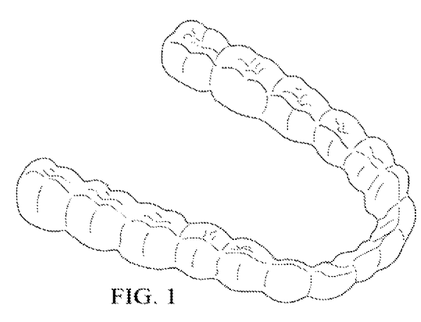
FIG. 1 shows a perspective view of a clear aligner. Only a single aligner for a single arch is shown, but they typically are used in pairs, one for each arch.
Figure 2A:
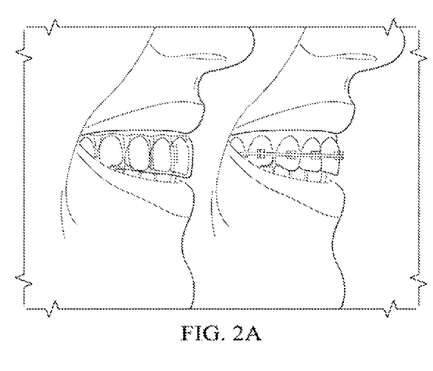
FIG. 2A-B shows a comparison of traditional braces versus the clear aligner. While a great improvement over braces, the clear aligner is still visible as a clear outline around the teeth.
Figure 2B:
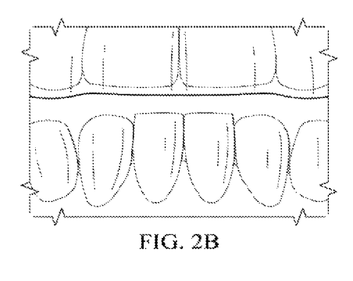
Figure 3:
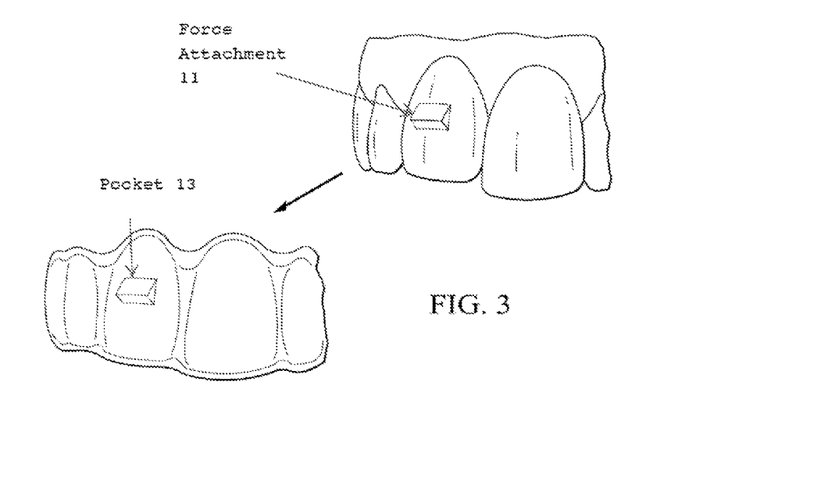
FIG. 3 shows an aligner with a pocket 13 formed for a clear force attachment 11. The force attachment thus provides a surface that the aligner can apply pressure to. If needed, a pressure point is built up inside the aligner to apply extra pressure to the raised force attachment.
Figure 4:
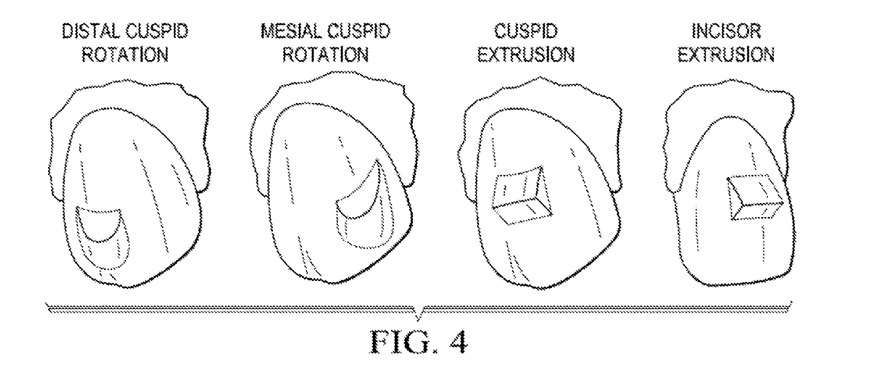
FIG. 4 shows an a variety of force attachments and their uses.
Figure 5:
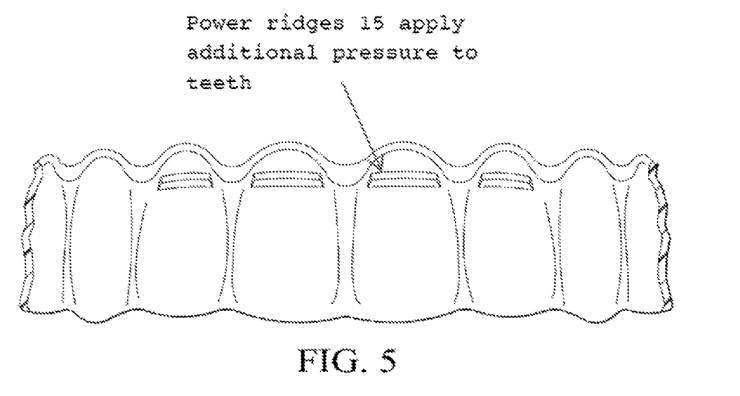
FIG. 5 shows a clear aligner with a inner ridge 15 positioned near the top of the crown, and which serves to apply additional forces. Such power ridges or other protrusions on the inner surface of an aligner can apply additional force directly to the teeth, or indirectly via force attachments shown in FIG. 4.
Figure 6:
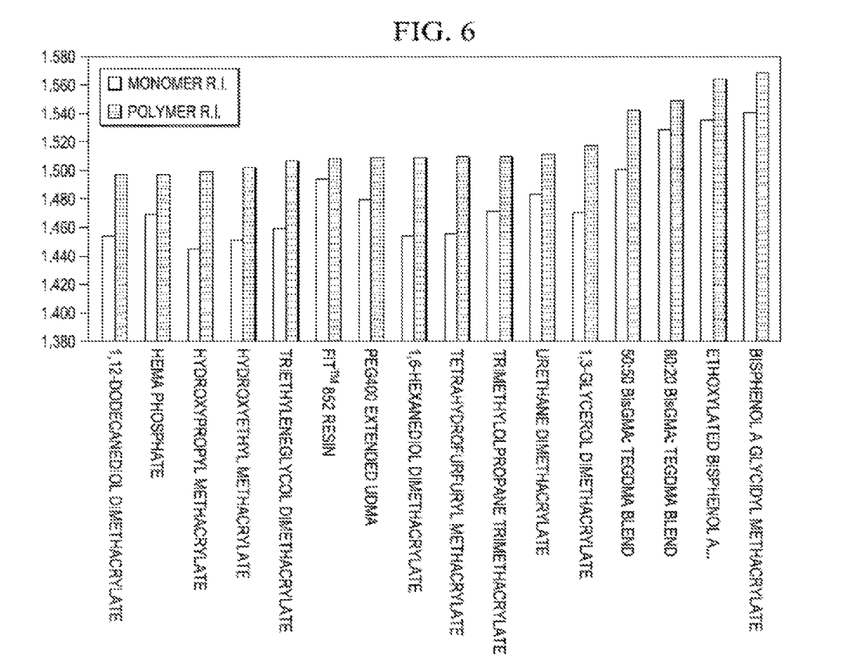
FIG. 6 shows the refractive index of several monomers and their resulting polymers.
Figure 7:
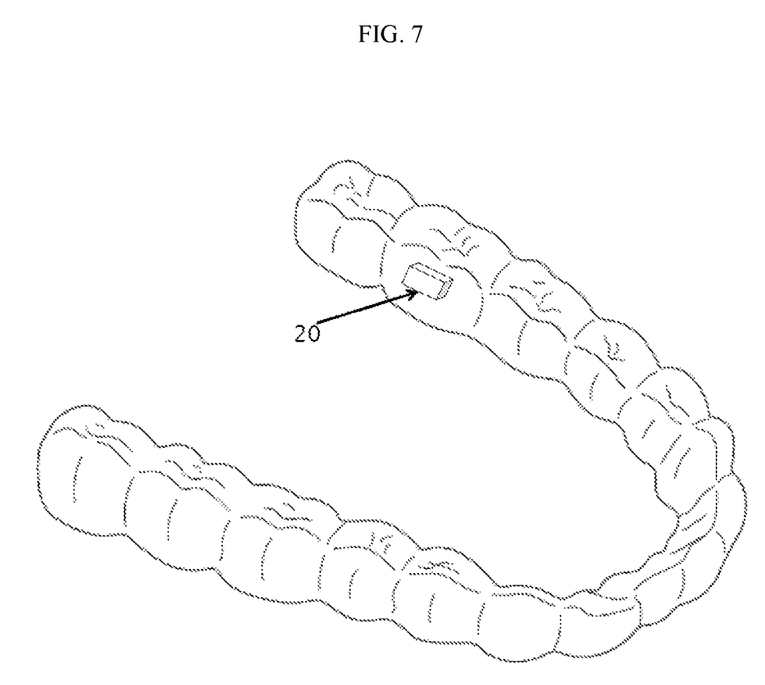
FIG. 7 shows a clear aligner having a power source/driver 20 positioned near the last molar on the lingual surface. The power source is operably coupled to a driver providing a second treatment modality selected from vibration, microcurrent, pulsed electromagnetic fields, or infrared light.

There is some affect on aesthetics, but because the force attachments are also clear, they are less noticeable from a distance. However, the aesthetics could be improved. Even the original clear aligner aesthetics could be improved because in use they produce a noticeable clear line under the teeth, which is easily seen when the patient is smiling (see FIG. 2A-B).

Yet another option is to combine the features of a clear aligner with some of the advantages of traditional appliance technology. Clear Fusion® Orthodontic Appliances, for example, combines Hawley appliances with clear aligner technology. For example, a rapid palatal expander can be combined with a clear aligner that interfaces with part of the dentition. Further, many practitioners have manually combined the aligner with various appliances, especially to treat class II malocclusions.

In addition to malocclusion, many patients have discolored or damaged teeth surfaces that need repair. The outer covering of the visible part of the tooth (the crown) is enamel, which is translucent and is white or bluish white or grey by itself, but with dentin underneath can vary in color from yellowish to grayish white. It is the hardest tissue in the human body and can endure crushing pressure of approximately 100,000 pounds per square inch. It consists of approximately 96% inorganic minerals—calcium and phosphorus (as hydroxyapatite)—as well as 1% organic materials and 3% water.

Like pearls, enamel is birefringent (thus can split a light beam into two colors) and has a refractive index of about 1.5-1.6 (in comparison porcelain is 1.5 and quartz is 1.54). However, refractive index will vary between patients, with wavelength used, the condition of the enamel, and with the measuring system used. Using optical coherence tomography (OCT), one group obtained the refractive index of dental enamel to be 1.631+/−0.007. Meng Z, et al., Measurement of the refractive index of human teeth by optical coherence tomography, J Biomed Opt. 14(3):034010 (2009).

Veneers are an important tool used to cover discolored or damaged teeth. A dentist or orthodontist may use one veneer to restore a single tooth that may have been fractured or discolored, or multiple teeth to create a "Hollywood" type of makeover. In terms of aesthetics, the ultimate in cosmetic dentisry is the porcelain veneer and/or crowns. Porcelain is a ceramic material made by heating raw materials, generally including clay in the form of kaolin, in a kiln to temperatures between 1,200° C. (2,192° F.) and 1,400° C. (2,552° F.). The toughness, strength, and translucence of porcelain arise mainly from the formation of glass and the mineral mullite within the fired body at these high temperatures. Porcelain has the translucent, yet white, appearance of real enamel, yet is longer lasting and more durable than the less expensive resins.

Clear aligners have been a tremendous improvement in orthodontic practice, as evidenced by their increasing market share and popularity with adult and to a lesser extent, teen, patients. However, further improvements in the aligner technology are always beneficial, and this application addresses some of those improvements. Improvements in aesthetics are particularly needed, because one of the most important impediments to orthodontic treatment is the perceived poor aesthetics during treatment, especially in teen and adult populations. See e.g., Klages, U., et al., American Journal of Orthodontics and Dentofacial Orthopedics 128(4): 442-449 (2005) ("favorable dental esthetics and previous orthodontic treatment might be important variables in explaining individual differences in oral-health attitudes and behaviors.").

SUMMARY OF THE INVENTION

The invention is directed to improved aligners with white coloration and thus have greatly improved aesthetics, especially when combined with force attachments. In preferred embodiments, the aligner has a pearlescent white color and thus has a luster equivalent to that of dental enamel.

The coloration can be achieved in a wide variety of ways:
1) add white or reflective pigments to the transparent resin used to manufacture the aligner
2) coat the inner surface of an existing aligner with a white coating
4) cover the aligners outer surface with an enamel or porcelain or ceramic coating
3) make the aligner with a 3D porcelain/ceramic printer or ceramic computer milling machine, thus making the aligner with naturally white materials
4) cover the outer surface of an aligner with a layer of solid veneer "Luster" (also spelled lustre) is the measurement of the quality and quantity of light that reflects from the surface and just under the surface of a pearl. It is essentially the reflective quality or brilliance of the surface of the pearl nacre. The more lustrous the pearl, the more it shines and reflects light and images. Pearls with low luster, in contrast, appear white or chalky, rather than brilliant and shiny. As used herein "pearlescent" means having the lustrous quality of a pearl, and is used interchangeably with luster or lustrous. Preferably, the pearlescent white pigments used herein have a refractive index of at least 0.03 higher than the refractive index of the resin alone, and is preferably at least about 1.5-1.6 or 1.50-1.63 when measured using visible light under wet conditions.

Although white may be a preferred color, other options may be desired, particularly amongst teen users. Thus, colored aligners of the invention can be modified for decorative or fashion uses or as a personality statement. Thus, the aligners can be colored for special occasions, e.g., team colors may be used for big games, black may be desirable for gothic users, long incisors and/or sparkly materials may be an option for a vampiric theme event. Alternatively, the aligners can be decorated, e.g., with a heart for Valentines Day, a star or flag. Pigments can either be added to the aligners for total coloring, or the aligners can be printed for particular designs.

As used herein, any reference to teeth, dentition, and the parts thereof is according to standard dental nomenclature. Thus, the occlusal surfaces of teeth are the bottoms of the teeth in the upper (maxillary) arch, and the tops of the teeth of the teeth in the lower (mandibular) arch, and the occlusal surfaces all together generally form a U-shape.

The facial surfaces are the vertical teeth surfaces on the face or cheek side, whereas the lingual surfaces are the vertical surfaces on the tongue or lingual side. The same reference surfaces occur in aligners and on the teeth, although aligners will have inner and outer surfaces since aligners are hollow.

The invention can comprise one or more of the following embodiments, in each possible combination:

An orthodontic remodeling device, comprising: an aligner having lingual, occlusal and facial surfaces, said aligner being shaped to intimately contact a plurality of teeth in an arch and apply sufficient pressure to at least one tooth in said arch to move said at least one tooth, wherein at least the facial surfaces of said aligner are a pearlescent white having a refractive index of at least 1.5 under visible light and wet conditions.

An improved orthodontic aligner, wherein an orthodontic aligner is shaped to intimately contact a plurality of teeth or all teeth in an arch and apply sufficient pressure to at least one tooth in said arch to move said tooth, the improvement comprising a pearlescent white pigment that is i) intimately admixed with a resin of said aligner or ii) in a coating on said aligner, such that said aligner has a pearlescent white coloration and an index of refraction of visible light of at least 1.5 when wet.

Orthodontic remodeling devices or aligners, wherein said lingual, occlusal and facial surfaces are each pearlescent white, on the outer surfaces thereof, on the inner surfaces thereof, in an interior layer thereof, or in their entireties.

Orthodontic remodeling devices or aligners, said aligner made with a transparent resin containing ceramic or porcelain or glass reflective particles or glass microspheres.

Orthodontic remodeling devices or aligners, said aligner comprising a resin and a pearlescent white coating or a transparent resin containing a pearlescent white pigment. The coating can be a veneer, applied as a solid shaped coating layer, or can be a pigment based coating that is applied as a liquid. Coatings can be further coated with clear coat.

The aligner can comprise a transparent resin and a pearlescent white coating or filler.

Orthodontic remodeling devices or aligners, said aligner comprises a transparent resin and a pearlescent white pigment applied as a coating or filler, said pearlescent white pigment having refractive index at least 0.03 greater than a refractive index of said transparent resin.

Orthodontic remodeling devices or aligners, wherein the aligner comprises a transparent resin and a pearlescent white pigment comprising a mica powder coated with titanium dioxide and/or iron oxide.

Orthodontic remodeling devices or aligners, said aligner made of a polyurethane resin with a pearlescent white pigment selected from the group consisting of amorphous ceramic particles, glass particles, 10-40 μm mica powder with $TiO_2$ and/or FeO coating, barium silicate particles, barium aluminosilicate particles, barium borosilicate particles, and strontium borosilicate particles.

Orthodontic remodeling devices or aligners, said pearlescent pigment being a mica powder coated with titanium dioxide or iron oxide or both, or being Novant Sirius S1510 Sparkle Pearl or Novant Sirius Flash Pearl Pearlescent Pigment.

Orthodontic remodeling devices or aligners, used together with force attachments that attach to a tooth and provide a surface that said aligner can apply force to.

Orthodontic remodeling devices or aligners, said aligner made of a polyurethane resin blended with a pearlescent white pigment selected from the group consisting of reflective particles of 10-40 μm, said particles selected from the group consisting of amorphous ceramic particles, glass particles, mica powder with $TiO_2$ and/or FeO coating, barium silicate particles, barium aluminosilicate particles, barium borosilicate particles, and strontium borosilicate particles.

Orthodontic remodeling devices or aligners, said aligner further comprising a power source operably coupled to a driver providing a second treatment modality selected from vibration, microcurrent, pulsed electromagnetic fields, or infrared light.

Methods of orthodontic remodeling are also provided, comprising wearing any of the aligners herein described for a period of time sufficient to affect orthodontic remodeling.

As used herein, the term "index of refraction" or "refraction index" refers to how light or any other radiation propagates through the medium and is defined as $$n=c/v$$

wherein n is the refraction index, c is the speed of light in vacuum, and v is the speed of light in the substance. Therefore, a refraction index of 1.33 means light travels 1.33 times slower in this substance than it does in vacuum. For visible light, most transparent media have refractive indices between 1 and 2.

The use of the word "a" or "an" when used in conjunction with the term "comprising" in the claims or the specification means one or more than one, unless the context dictates otherwise.

The term "about" means the stated value plus or minus the margin of error of measurement or plus or minus 10% if no method of measurement is indicated.

The use of the term "or" in the claims is used to mean "and/or" unless explicitly indicated to refer to alternatives only or if the alternatives are mutually exclusive.

The terms "comprise", "have", "include" and "contain" (and their variants) are open-ended linking verbs and allow the addition of other elements when used in a claim.

The phrase "consisting of" is closed, and excludes all additional elements.

The phrase "consisting essentially of" excludes additional material elements, but allows the inclusions of non-material elements that do not substantially change the nature of the invention. Thus, the term consisting essentially of excludes only material elements, such as non-retainer-like treatment modalities.

The following abbreviations are used herein:

| Abbreviation | Expansion |
| --- | --- |
| TEGDMA | Triethylene glycol dimethacrylate |
| BIS-GMA | Bisphenol A glycidyl methacrylate |
| PS | Polystyrene |
| PP | Polypropylene |
| PE | Polyethylene |
| PVC | Polyvinyl chloride |
| PU | polyurethane |

DETAILED DESCRIPTION OF THE INVENTION

The invention is a pearlescent white aligner. Such aligners can hide force attachments and avoid the appearance of a thin clear lines under the occlusal edges of teeth and in front of the facial surfaces. The aligners thus have potentially even better aesthetics than a patients own teeth, which may be discolored or unevenly colored. Greatly improved aesthetics will aid practitioners in capturing that portion of the market that is still very resistant to orthodontic treatment, and will allow many adult and teen patients the comfort of improved aesthetics during a lengthy treatment period.

Preferably, the index of refraction of a pearlescent white aligner will be at least 0.03 greater than that of the transparent resin alone, and can be 0.04 greater, but too much shine does not look natural. Overall, the aligner should have an index of refraction of at least about 1.5-1.6 or slightly higher. Aligners can also be covered with a clear or translucent coating for better aesthetics if the material is insufficiently lustrous.

Aligners can be made according to any existing or future developed technology, include wax impressions, but more preferably are made using state-of-the-art 3D scanning and modeling software. Indeed, the art for making aligners and positions is quite extensive, as described in US20090191503, US20100055635, U.S. Pat. No. 3,660,900, U.S. Pat. No. 3,860,803, U.S. Pat. No. 4,755,139, U.S. Pat. No. 4,798,534, U.S. Pat. No. 4,856,991, U.S. Pat. No. 4,936,862, U.S. Pat. No. 5,011,405, U.S. Pat. No. 5,035,613, U.S. Pat. No. 5,055,039, U.S. Pat. No. 5,059,118, U.S. Pat. No. 5,139,419, U.S. Pat. No. 5,186,623, U.S. Pat. No. 5,273,429, U.S. Pat. No. 5,338,198, U.S. Pat. No. 5,340,309, U.S. Pat. No. 5,342,202, U.S. Pat. No. 5,368,478, U.S. Pat. No. 5,382,164, U.S. Pat. No. 5,395,238, U.S. Pat. No. 5,431,562, U.S. Pat. No. 5,447,432, U.S. Pat. No. 5,452,219, U.S. Pat. No. 5,454,717, U.S. Pat. No. 5,474,448, U.S. Pat. No. 5,533,895, U.S. Pat. No. 5,549,476, U.S. Pat. No. 5,587,912, U.S. Pat. No. 5,605,459, U.S. Pat. No. 5,607,305, U.S. Pat. No. 5,645,421, U.S. Pat. No. 6,471,511 U.S. Pat. No. 6,682,346 U.S. Pat. No. 6,699,037, U.S. Pat. No. 7,481,121, each incorporated herein by reference.

The aligners may be made of any suitable material, including polyesters, polyvinyl chlorides, polycarbonate, polyacrylates, silicone, and the like, but preferred materials include polyurethane, especially USP Class VI medical-grade, high molecular weight, polyurethane resins with methylene diphenyl diisocyanate and 1,6-hexanediol.

Resins can be made to appear pearlescent with the addition of pigments, glass, porcelain or ceramic particles, and the like. For example, mica powder coated by titanium oxide produces a pearlescent luster, and increasing the mica powder's particle size will increase the luster. The best pearl lustre, brightness, and colour intensity occurs with mica platelets that are 10 to 40 µm in size, while larger platelets of 50 to 150 µm confer sparkle and glitter.

Mica-based pearlescents can be used in nearly all thermoplastics and most processes. Their effects are most intense in transparent resins like PS, PP, PE, PVC, acrylic, styrene block copolymers, and silicone. Pearlescents can also be incorporated in many thermosets, including unsaturated polyester, acrylic, urethane, and epoxy.

Pearlescent pigments can be master batched containing 25% pearlescent pigments (up to 50%) in most resins by drum tumbling or mixing in twin-shell, ribbon, or high-speed blenders. Pearlescent pigments should not be ground or subjected to extended cycles or heavy shear because these can shear off the metal oxide cladding and damage the platelets. Banbury-type or continuous mixers are most often used to create pearlescent master batches, although two-roll mills, calenders, vertical intensive mixers, and double planetary mixers are also suitable as long as excessive shear is avoided. Pearlescent pigments are usually incorporated in powdered polymers such as PVC and PE by simple blending. Blending usually begins with organic pigments, followed by inorganic pigments, and lastly the pearlescent pigments.

Highly filled plastics are not good candidates for pearlescent pigments because opaque fillers scatter light, eliminating the pearlescent effect. Thus, it is best to limit fillers to less than 1% or 2% in systems containing pearl pigments.

Dispersion aids, if needed, include low-molecular-weight polyethylene waxes and calcium or magnesium stearate. Moulders often add 1% LMW-PE wax to polyolefins and mix for 20-30 min. With PS they typically use only about 0.1% of a dispersion aid.

Pearlescent white pigments are available from many commercial suppliers. For example, KTZ® provides mica substrate coated with titanium dioxide and/or iron oxide to create pearlescent effects, and their pigments are safe for costmetic uses. Novant also has pearlescent pigments. For example, the Novant Sirius Silver White Series is based on a thin layer of rutile or anatase titanium dioxide on mica. Preferred pigments include Novant Sirius S1510 Sparkle Pearl and Novant Sirius Flash Pearl Pearlescent Pigment, both of which are transparent, and show no toxicity and no stimulative effects on skin and mucous membrane.

A wide variety of pearlescent coatings are also available, including Ceramcoat Pearl Luster Medium by Delta Creative, Pearlie by Booth Elliot & CO., and many companies offer customized coatings, including thin-coat materials. The coatings can be applied to the inside of the aligner, but are preferably applied to at least the outer, facial surface. A pearlescent coating can also be covered with another clear coat, for longevity, additional luster and to reduce patient exposure to the coating.

One coating material is described in U.S. Pat. No. 7,214,262, which describes a transparent resin matrix containing embedded glass microspheres. The refractive index of the microspheres is at least 0.03 greater than the refractive index of the transparent resin matrix, so that incoming light is reflected back in the same direction as it was emanated, providing a lustrous dental coating that is cosmetically appealing and covers dental defects and discoloration. The transparent resin matrix with glass microspheres is formed by mixing together a methacrylate based liquid monomer of methyl methacrylate or BIS-GMA and glass microspheres coated with activators/catalysts. Although the coating provided therein is temporary, a longer lasting material could be made by changing the polymeric base and/or crosslinkers. Indeed, these glass microspheres can be added directly to the resin base of the aligner.

Other patents describe similar technology. For example, a composite dental coating is described at US20090047633, which has nanometer sized silica particles in a light curable polymeric base. U.S. Pat. No. 6,899,948 discloses dental materials comprising a hardenable resin and "nano-sized"

(<200 nm) silica particles dispersed within the resin. The nano-sized silica particles are further described as being discrete and non-agglomerated and in a dry powder form. The material is suitable in a variety of dental applications, including to make veneers, crowns and dentures.

U.S. Pat. No. 6,797,767 discloses polymerizable composite materials that can be used as dental restoratives, bonding agents and adhesives. The material comprises at least one multifunctional acid containing monomer such as bis-2 (methacryloxy)ethyl phosphate; a non-reactive filler such as micron or submicron-sized particles of silica; a polymerization system capable of being activated by light to polymerize the composite material; and water. The composite material is light cured.

In fact, a great many glass fillers are available and some fillers and their index of refraction are given in the Table:

| Glass Filler | Index of Refraction |
|---|---|
| Barium Silicate | 1.540 |
| Barium Aluminosilicate | 1.580 |
| Barium Borosilicate | 1.553 |
| Strontium Borosilicate | 1.500 |

In other embodiments, the aligner can have a veneer or be entirely created from a veneer-like material. Porcelains are preferred, as having good strength, stain resistance and luster, but glassy ceramics or composites can also be used. Porcelain and ceramic materials can have a biocompatible resin coating, at least on an inner surface of the aligner, for patient comfort.

U.S. Pat. No. 7,229,286, for example, describes a veneer composite having a glass-ceramic base or coping and a resin composite material in the form of a veneer bonded to the coping. Preferred glass-ceramic materials are $Li_2O$—$CaO$—$Al_2O_3$—$SiO_2$—X, $Al(PO_3)_3$—$SiO_2$—$Li_2O$—CaX and $Li_2O$—ZnO—$P_2O_5$—X, where X is a network modifier such as $TiO_2$, $ZrO_2$, $La_2O_3$, $CeO_2$, $Y_2O_3$, ZnO, MgO, BaO, PbO, $Ta_2O_5$, $Li_2O$, $K_2O$, $CaF_2$, $MgF_2$, $AlF_3$, $BaF_2$, and $Na_2O$. Preferred veneering materials include composites with dimethacrylate matrix resins. These matrix resins are generally mixtures of BIS-GMA and TEGDMA, in many commercial material, however urethane dimethacrylates and large oligomeric structures of BIS-GMA-urethanes may also be used.

Alternatively, a porcelain or ceramic veneer for the aligner can be made, e.g., using a CEREC porcelain milling computer available from Sirona®, and the veneer bonded to a clear aligner. Porcelain materials can be any suitable porcelain, but is preferably the Cerinate porcelain, available at Den-Mat Corporation, e.g., U.S. Pat. No. 5,009,709. A thin (<0.5 mm) layer is applied, preferably <0.2 mm in thickness. Thinner materials can be used in the invention, e.g., 0.1 mm thick veneers, because they are supported on the aligner base and need only last 1-2 weeks before the aligner is changed out. In contrast, veneers need to last a decade or more, and thus need to be thicker.

U.S. Pat. No. 4,475,892 describes microcellular ceramic material comprising a plurality of elongated vitreous micro-sized ceramic rods which are placed in side-by-side touching relation and define elongated lines of contact therebetween. The rods also define interstices therebetween which may be void or may be filled or substantially filled with vitreous fibers, polymer materials, acid soluble or insoluble vitreous fibers and other suitable fibers. The rod mass either so filled or unfilled is first fused at the lines of rod contact by elevated temperature and is then annealed to cause the ceramic fibers to crystallize and form an elongated porous crystalline log. The log is then sectioned transversely or linearly to form thin wafers which in turn are built up in layers which are fused to form useful integral composite cellular objects, such as dental veneers.

Ceramics can vary from being very translucent to very opaque. In general, the glassier the microstructure (noncrystalline), the more translucent the ceramic will appear; the more crystalline, the more opaque. Other contributory factors to translucency include particle size, particle density, refractive index, and porosity, to name a few. Both feldspathic porcelain and glass-infiltrated ceramics presented long-term veneer survival rates of about 96%-98% in 5 years.

In one embodiment, the entire aligner can be made of ceramic, using e.g., CEREC porcelain milling computer or 3D printing technology, and the ceramic can be coated with a clear coat for a smooth, comfortable, sealed surface texture. Ceramics by themselves tend to be brittle, however, ceramics can be made more flexible by combining them with other materials, such as an organic binding matrix or zirconium oxides and similar oxides. E.g., U.S. Pat. No. 5,089,455, U.S. Pat. No. 6,354,144.

PorcelainCeRam-Kote 54® is a flexible ceramic coating that is highly adhesive and when fully cured is food safe. Keraflex porcelain tape, is another example of a flexible porcelain in an organic matrix. It is as flexible as rubber, and can be pressed into shape, yet results in strong and translucent pure porcelain when fired to cone 10.

Other ceramics are known and used for dental restorative purposes. For example, Shofu's Ceramage®, a zirconium silicate micro-ceramic has virtually the same light transmission as natural teeth and have remarkable translucency. Lava Zirconia offers strength and longevity, excellent fit, and higher translucency and restoration esthetics. NobelProcera™ Crown Alumina provides an optimal all-ceramic strength with excellent aesthetics.

While veneers and/or ceramic aligners may be the ultimate in providing a realistic tooth-like aligner appearance, they may also be of higher expense than pigments and/or coatings. Therefore, coatings and/or pigments may be preferred.

However, yet another option is to mix ceramics with a resin matrix, thus achieving a flexible aligner, with the translucency and color of real teeth. Polymer ceramic materials are inorganic-organic composites consisting of ceramic fillers and a matrix of organic polymers—particularly polysiloxanes. The formation of polymer ceramics is based on thermal curing of functionalized resins being able to form ceramic-like structures in the result of heat treatment above 200° C. Polymer-ceramics can be processed by a broad variety of plastic forming techniques like high pressure injection molding or extrusion. Polymer-ceramic composites are characterized by high thermal stability, low shrinkage, high stability of shape, and high dimensional accuracy. Relevant usage properties and processing parameters can also be adjusted by the choice of appropriate functional fillers, binder systems, and plasticizing additives. Indeed, composites are already preferred for use in manufacturing dentures because of the increased flexibility over pure porcelains, and thus longer wear. Tarazzo et al., Comparison of retentive systems for composites used as alternatives to porcelain in fixed partial dentures The Journal of Prosthetic Dentistry 89(6): 572-578 (2003).

Another option is an interpenetrating polymer network (IPN), which is a material containing two polymers, each in network form. In biomaterials used in dentistry, the IPN-like nanostructures are used in denture base polymers, denture teeth and fibre-reinforced composites. IPN structures provide the specific and desired properties for the resin system prior to and after polymerization. At adhesive interfaces, IPN polymers and composites provide good interfacial adhesion for adhering and veneering resin composites based on the so-called secondary-IPN bonding formation due to swelling of the IPN nanostructure.

Yet another option is a laminate structure, such as those found in veneer laminates. E.g., U.S. Pat. No. 4,433,959.

Additional information on suitable dental materials is readily available. See e.g., Basic Dental Materials By Manappallil (3d Ed. 2008). Pini N., et al., Advances in dental veneers: materials, applications, and techniques, Clinical, Cosmetic and Investigational Dentistry 4:9-16 (2012). Thus, one of skill in the art can appreciate that there are a great many dental materials available for creating a thin, strong, yet somewhat flexible aligner with pearlescent white coloring.

The aligners of the invention can be used for any orthodontic remodeling application, and are particularly useful when combined with force attachments. The aligners can also be combined with other treatment modalities, such as vibration, pulsed magnetic fields, or pulsed microcurrents, infrared light, all of which are known to speed orthodontic remodeling. See e.g., 60/906,807, US20080227046, US20080227047, US20100055634, 61/624,242, PCT/US13/36289, US20110136070, US20120040300, US20130322018 and US20130059263, 61/673,236, all by OrthoAccel Technologies Inc. and describing how these modalities can be combined with aligner technology, as well as with fluoride releasing materials in 61/769,507.

Each of the following is incorporated by reference in its entirety.

60/906,807, US20080227046, US20080227047, US20100055634, 61/624,242, PCT/US13/36289, US20110136070, US20120040300, US20130059263 and US20130322018, Ser. No. 13/850,151, filed Mar. 25, 2013, 61/673,236, 61/769,507.

US20090191503, US20100055635, U.S. Pat. No. 3,660,900, U.S. Pat. No. 3,860,803, U.S. Pat. No. 4,755,139, U.S. Pat. No. 4,798,534, U.S. Pat. No. 4,856,991, U.S. Pat. No. 4,936,862, U.S. Pat. No. 5,011,405, U.S. Pat. No. 5,035,613, U.S. Pat. No. 5,055,039, U.S. Pat. No. 5,059,118, U.S. Pat. No. 5,139,419, U.S. Pat. No. 5,186,623, U.S. Pat. No. 5,273,429, U.S. Pat. No. 5,338,198, U.S. Pat. No. 5,340,309, U.S. Pat. No. 5,342,202, U.S. Pat. No. 5,368,478, U.S. Pat. No. 5,382,164, U.S. Pat. No. 5,395,238, U.S. Pat. No. 5,431,562, U.S. Pat. No. 5,447,432, U.S. Pat. No. 5,452,219, U.S. Pat. No. 5,454,717, U.S. Pat. No. 5,474,448, U.S. Pat. No. 5,533,895, U.S. Pat. No. 5,549,476, U.S. Pat. No. 5,587,912, U.S. Pat. No. 5,605,459, U.S. Pat. No. 5,607,305, U.S. Pat. No. 5,645,421, U.S. Pat. No. 6,471,511 U.S. Pat. No. 6,682,346 U.S. Pat. No. 6,699,037, U.S. Pat. No. 7,481,121, U.S. Pat. No. 7,214,262, US20090047633, U.S. Pat. No. 6,899,948, U.S. Pat. No. 6,797,767, U.S. Pat. No. 7,229,286, U.S. Pat. No. 4,475,892, U.S. Pat. No. 5,009,709, U.S. Pat. No. 5,089,455, U.S. Pat. No. 6,354,144, U.S. Pat. No. 4,433,959

Tarazzo et al., Comparison of retentive systems for composites used as alternatives to porcelain in fixed partial dentures The Journal of Prosthetic Dentistry 89(6): 572-578 (2003).

Basic Dental Materials, by Manappallil (3d Ed. 2008).

Pini N., et al., Advances in Dental Veneers: Materials, Applications, and Techniques, Clinical, Cosmetic and Investigational Dentistry 4:9-16 (2012). Thus, one of skill in the art can appreciate that there are a great many dental materials available for creating a strong, flexible aligner with pearlescent white coloring.

While the invention is described above in detail, it should be understood that various changes, substitutions, and alterations can be made without departing from the spirit and scope of the invention as defined by the following claims. Those skilled in the art may be able to study the preferred embodiments and identify other ways to practice the invention that are not exactly as described herein. It is the intent of the inventors that variations and equivalents of the invention are within the scope of the claims while the description, abstract and drawings are not to be used to limit the scope of the invention. The invention is specifically intended to be as broad as the claims below and their equivalents.

What is claimed is:

1. An orthodontic remodeling device, comprising:
   a) an aligner made of a polyurethane resin and having lingual, occlusal and facial surfaces,
   b) said aligner being shaped to intimately contact a plurality of teeth in an arch and apply sufficient pressure to at least one tooth in said arch to move said at least one tooth,
   c) wherein at least the facial surfaces of said aligner are a pearlescent white having a refractive index of 1.5-1.63 under visible light and wet conditions.

2. The orthodontic remodeling device of claim 1, wherein said lingual, occlusal and facial surfaces are each pearlescent white.

3. The orthodontic remodeling device of claim 1, said aligner made with a transparent resin containing ceramic or porcelain or glass reflective particles.

4. The orthodontic remodeling device of claim 1, said aligner made with a transparent resin containing glass microspheres.

5. The orthodontic remodeling device of claim 1, said aligner comprising a resin and a pearlescent white coating or a transparent resin containing a pearlescent white pigment filler.

6. The orthodontic remodeling device of claim 1, said aligner comprises a transparent resin and a pearlescent white pigment applied as a coating or a filler.

7. The orthodontic remodeling device of claim 1, said aligner comprises a transparent resin and a pearlescent white pigment coating or filler, said pearlescent white pigment having refractive index at least 0.03 greater than a refractive index of said transparent resin.

8. The orthodontic remodeling device of claim 1, said aligner comprises a transparent resin and a pearlescent white pigment comprising a mica powder coated with titanium dioxide or iron oxide.

9. The orthodontic remodeling device of claim 5, further comprising a clear coating over an outermost layer of said aligner.

10. The orthodontic remodeling device of claim 1, said aligner made of a polyurethane resin with a pearlescent white pigment selected from the group consisting of amorphous ceramic particles, glass particles, 10-40 μm mica powder with $TiO_2$ and/or FeO coating, barium silicate particles, barium aluminosilicate particles, barium borosilicate particles, and strontium borosilicate particles.

11. An improved orthodontic aligner, the orthodontic aligner shaped to intimately contact a plurality of teeth or all teeth in an arch and apply sufficient pressure to at least one tooth in said arch to move said tooth, the improvement comprising a pearlescent white pigment that is i) intimately admixed with a polyurethane resin of said aligner or ii) in a coating on a polyurethane resin of said aligner, such that said aligner has a pearlescent white coloration and an index of refraction of visible light of 1.5-1.63 when wet.

12. The improved orthodontic aligner of claim 11, said pearlescent pigment being a mica powder coated with titanium dioxide or iron oxide or both.

13. The improved orthodontic aligner of claim 11, wherein the aligner is capable of being used together with force attachments that are adapted to attach to a tooth and provide a surface that said aligner can apply force to.

14. The improved orthodontic aligner of claim 11, said aligner made of a polyurethane resin blended with a pearlescent white pigment selected from the group consisting of reflective particles of 10-40 μm, said particles selected from the group consisting of amorphous ceramic particles, glass particles, mica powder with $TiO_2$ and/or FeO coating, barium silicate particles, barium aluminosilicate particles, barium borosilicate particles, and strontium borosilicate particles.

15. A method of orthodontic remodeling comprising wearing the aligner of claim 1 for a period of time sufficient to affect orthodontic remodeling.

16. A method of orthodontic remodeling comprising wearing the aligner of claim 11 for a period of time sufficient to affect orthodontic remodeling.

* * * * *